United States Patent [19]

Huston et al.

[11] Patent Number: 5,606,163
[45] Date of Patent: Feb. 25, 1997

[54] ALL-OPTICAL, RAPID READOUT, FIBER-COUPLED THERMOLUMINESCENT DOSIMETER SYSTEM

[75] Inventors: Alan L. Huston; Brian L. Justus, both of Springfield, Va.

[73] Assignee: The United States of America as represented by the Secretary of the Navy, Washington, D.C.

[21] Appl. No.: 371,305

[22] Filed: Jan. 11, 1995

[51] Int. Cl.$^6$ .............................. G01T 1/115; G01T 1/105
[52] U.S. Cl. .................. 250/337; 250/484.3; 250/484.5
[58] Field of Search ................ 250/337, 483.1, 250/484.2, 484.3, 484.4, 484.5

[56]  References Cited

U.S. PATENT DOCUMENTS

| | | | |
|---|---|---|---|
| 2,902,605 | 9/1959 | Wallack | 250/337 |
| 4,448,547 | 5/1984 | Wickesheim | 374/131 |
| 5,030,834 | 7/1991 | Lindmayer et al. | 250/484.1 |
| 5,091,653 | 2/1992 | Creager et al. | 250/484.1 |
| 5,446,286 | 8/1995 | Bhargava | 250/361 R |

*Primary Examiner*—Constantine Hannaher
*Attorney, Agent, or Firm*—Thomas McDonnell; George Jameson

[57]  ABSTRACT

A thermoluminescent radiation dosimeter system for the remote monitoring of radiation sources. The system includes a radiation-sensitive thermoluminescent dosimeter which utilizes a new, semiconductor-doped glass material disposed at a remote location for storing energy from ionizing radiation when exposed thereto and for releasing the stored energy in the form of thermoluminescence light at a first wavelength when stimulated by exposure to light energy at a predetermined stimulating second wavelength. The system further includes: an optical source for providing stimulating light energy at the predetermined stimulating second wavelength; a thermoluminescent detector for measuring thermoluminescent emissions; and an optical fiber for passing the predetermined stimulating light energy from the optical source to the thermoluminescent dosimeter to stimulate the thermoluminescent dosimeter to produce thermoluminescence light from stored energy and for passing the thermoluminescence light to the thermoluminescent detector to enable the thermoluminescent detector to measure any thermoluminescent emissions occuring when the thermoluminescent dosimeter is heated by the light energy at the predetermined stimulating second wavelength.

12 Claims, 8 Drawing Sheets

FIG. 12

ALL-OPTICAL, RAPID READOUT, FIBER-COUPLED THERMOLUMINESCENT DOSIMETER SYSTEM

CROSS-REFERENCE TO RELATED APPLICATIONS

This application is related to commonly assigned U.S. application Ser. No. 08/371,306 entitled "Glass Matrix Doped With Activated Luminescent Nanocrystalline Particles", filed on even date herewith by Brian L. Justus and Alan L. Huston, the entirety of which is incorporated by reference herein for all purposes.

BACKGROUND OF THE INVENTION

1. Field of the Invention

The present invention relates to dosimeters and particularly to a new type of rapid-readout, thermoluminescent dosimeter for the remote monitoring of radiation sources, such as ultraviolet, x-ray or gamma radiation, using a radiation-sensitive glass material (dosimeter) in conjunction with fiber optic components.

2. Description of the Related Art

Thermoluminescent (TL) materials have been used for many years to monitor radiation exposure levels. These dosimeters measure the accumulated radiation exposure over a period of time, ranging from minutes, to days to years. Materials such as metal-ion-activated Lithium Fluoride (LiF), or Calcium Fluoride ($CaF_2$) are commonly used in "film badges" to monitor personnel exposure to radiation. These materials are generally prepared from powders that are pressed into opaque white pellets. When exposed to ionizing radiation, such as deep ultraviolet, x-ray or gamma radiation, free electrons are generated and are trapped in the material. The electrons remain trapped until a source of heat is applied to the material to stimulate the release of the electrons. The electrons recombine with an ion in the material resulting in the emission of light. The amount of light emitted is proportional to the amount of radiation exposure.

Thermoluminescent dosimetry (TLD) materials that are used in practice are generally limited in size because of the high degree of light scattering. Only light generated near the surface can be effectively used to measure radiation dosages. As a result, commonly used commercial dosimetry materials have dimensions of approximately 2 mm×2 mm×0.2 mm. This small size limits the dynamic range and ultimate sensitivity of the material.

The traditional approach to TLD involves the collection of the dosimeter material from a film badge or other monitoring package and placement of the material inside a machine that heats the sample at a controlled rate and monitors the light emission as a function of temperature.

Glass materials have been studied for radiation dosimetry measurements. With some glasses, radiation exposure leads to darkening of the glass and the degree of darkening is used as a measure of the radiation dose. Thermoluminescent glasses have also been reported. The effectiveness of these glasses for TLD applications has been limited for a number of reasons, including low readout temperatures, low sensitivity compared to crystalline phosphors and low saturation doses.

Fiber optic TLD systems have also been described. One system utilizes traditional TL phosphors attached to the end of a 0.6 mm diameter optical fiber. An absorbing material is applied to one surface of the phosphor and a diode laser is used to heat the absorber which in turn heats the TL material by diffusive heating. This system is described as a remote fiber optic laser TLD system. The performance of the system is limited in several ways. First, the TL material must be very thin, approximately 0.1 mm, to allow the laser heating source to be transmitted through the TL material to the absorber material. As a consequence, in order to attain sufficient TL sensitivity, the diameter of the TL material must be fairly large. The diameter of the optical fiber must also be large to match the size of the TL dosimeter. Applications that involve in vivo monitoring of radiation exposure in the human body via fiber catheterization can be improved if smaller fibers can be used.

A laser heating method has been described for the heating of TL materials stacked in layers. In this study, a $CO_2$ laser was used as the heat source. This does provide for rapid, efficient heating but is impractical for fiber optic applications because ordinary optical fibers are not transparent to $CO_2$ laser wavelengths, and specialty, $CO_2$-transmitting fibers are of limited utility, having large diameters (0.7 to 2 mm diameter), limited transparency for visible light wavelengths that correspond to the thermoluminescence and are very expensive (one meter of fiber costs approximately $1000, 10 meters cost $5500).

SUMMARY OF THE INVENTION

It is therefore an object of the invention to provide an improved dosimeter.

Another object of the invention is to provide a dosimeter apparatus for the remote monitoring of radiation sources such as deep ultraviolet, x-ray and gamma radiation.

A further object of the invention is to provide a rapid-readout, thermoluminescent dosimeter for the remote monitoring of radiation sources using a radiation-sensitive glass material (dosimeter) in conjunction with fiber optic components.

These and other objects of this invention are achieved by providing a thermoluminescent radiation dosimeter system comprising: a radiation-sensitive thermoluminescent dosimeter which utilizes a new, semiconductor-doped glass material disposed at a remote location for storing energy from ionizing radiation when exposed thereto and for releasing the stored energy in the form of thermoluminescence light at a first wavelength when stimulated by exposure to light energy at a predetermined stimulating second wavelength; an optical source for providing stimulating light energy at the predetermined stimulating second wavelength; a thermoluminescent detector for measuring thermoluminescent emissions at the first wavelength; and an optical fiber for passing the predetermined stimulating light energy from the optical source to the thermoluminescent dosimeter to stimulate the thermoluminescent dosimeter to produce thermoluminescence light from stored energy and for passing the thermoluminescence light to the thermoluminescent detector to enable the thermoluminescent detector to measure any thermoluminescent emissions occuring when the thermoluminescent dosimeter is heated by the light energy at the predetermined stimulating second wavelength.

BRIEF DESCRIPTION OF THE DRAWINGS

These and other objects, features and advantages of the invention, as well as the invention itself, will become better understood by reference to the following detailed description when considered in connection with the accompanying drawings wherein like reference numerals designate identical or corresponding parts throughout the several views and wherein.

DETAILED DESCRIPTION OF THE PREFERRED EMBODIMENTS

The thermoluminescent dosimeter system described in this invention utilizes a novel, semiconductor-doped glass material that was recently developed by the present inventors and described in the above-noted U.S. application Ser. No. 08/371,306. One particular formulation of this semiconductor-doped glass material consists of nanometer-sized, zinc sulfide crystals, activated with copper ions. Exposure to ionizing radiation, such as deep ultraviolet, x-ray or gamma radiation, results in the formation of trapped electrons in the composite glass material. The electrons remain trapped until the temperature of the material is raised to approximately 150 degrees C. At this temperature, some of the trapped electrons recombine with the copper ions, producing green light with a wavelength of approximately 500 nanometers (nm). It is assumed that the thermoluminescence spectrum is similar to the ultraviolet (UV) excited photoluminescence spectrum.

Figure 1:
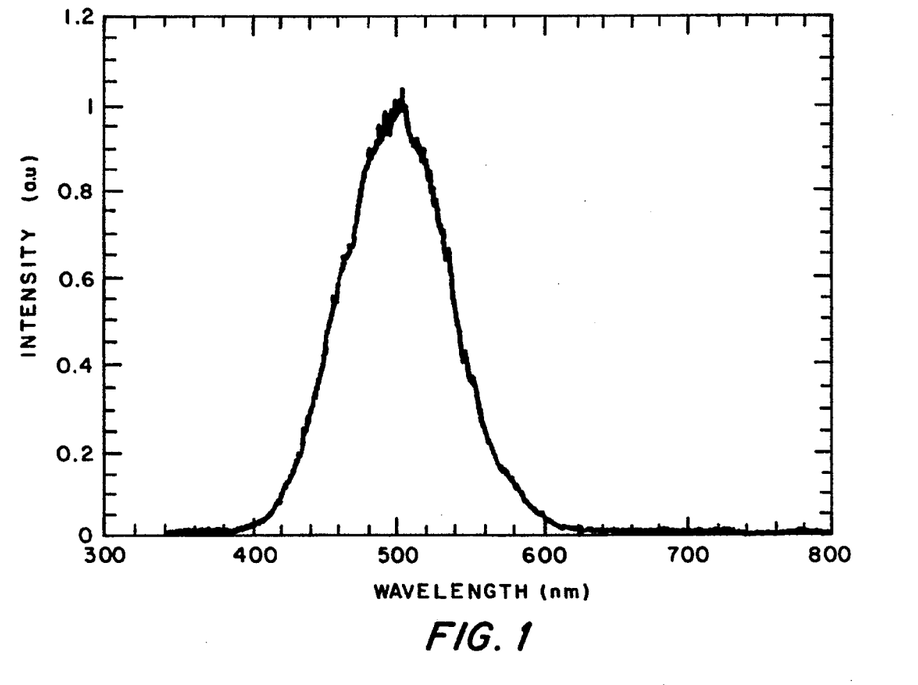
FIG. 1 illustrates the wavelength spectrum of ZnS:Cu photoluminescence.

FIG. 1 shows the photoluminescence spectum of an exemplary material, zinc sulfide (ZnS) doped with copper (Cu) nanocrystals (ZnS:Cu), in a Vycor™ glass excited with a laser pulse (to be discussed). Although this is the photoluminescence spectum, this is essentially the same spectral output as the thermoluminescence that is observed using the thermoluminescence dosimeter of the invention (described in relation to FIG. 5).

The wavelength range in FIG. 1 that is emitted by this exemplary ZnS:Cu semiconductor-doped glass material is good for commercial thermoluminescence measuring devices. Most of such devices are sensitive to wavelengths in this wavelength range. Redder wavelengths are often not preferred due to interference with black-body emission, but they can be used. The dosimeter system of the invention can be modified to read redder emissions. The exemplary ZnS:Cu semiconductor-doped glass material absorbs ultraviolet light at about 266 nanometers (nm) and, as indicated in FIG. 1, emits that photoluminescence in a broadband ranging from about 400 nm to about 620 nm and has a peak intensity at about 500 nm (with a color that appears to be blue-green).

Figure 2:
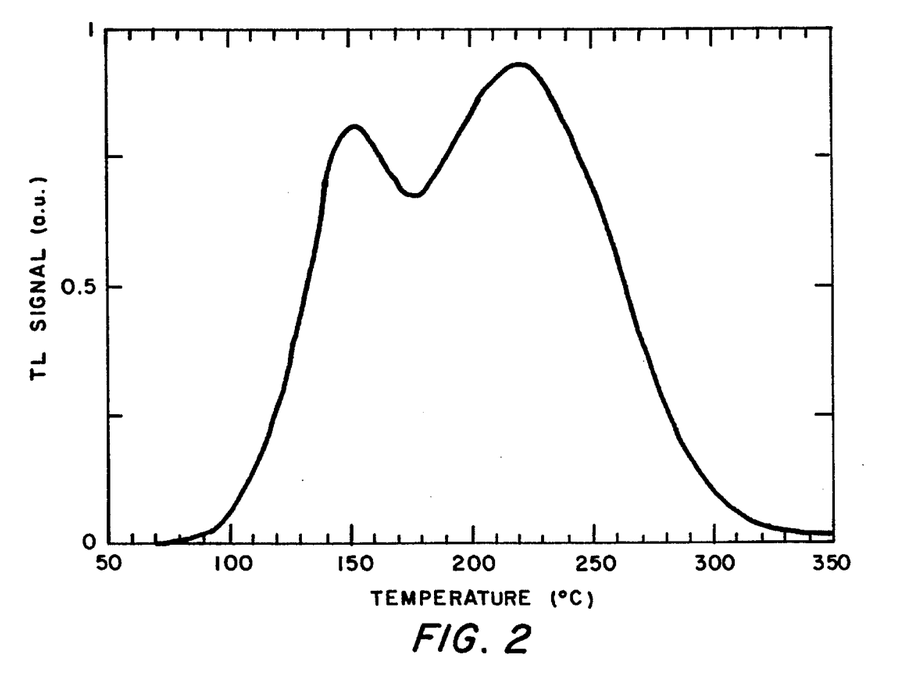
FIG. 2 illustrates the intensity of the thermoluminescent light emission of ZnS:Cu as a function of temperature.

FIG. 2 shows the intensity of the thermoluminescence emission from the exemplary ZnS:Cu semiconductor-doped glass material as a function of the temperature. More specifically, FIG. 2 shows the thermoluminescence glow curve of the ZnS doped with Cu in Vycor™ glass after being exposed to 20 grays (Gy) exposure of, for example, cobalt 60 gamma radiation. The spectrum shown in FIG. 2 was then obtained by heating the exemplary ZnS:Cu semiconductor-doped glass material at a constant rate over the temperature range from about 50 degrees centrigrade(C) to about 350 degrees C. and then measuring the thermoluminescence output with a photomultiplier tube (not shown).

The glow curve of FIG. 2 shows a beginning of the thermoluminescent (TL) signal at approximately 100 degrees C. and then two peaks. A first peak occurs at approximately 160 degrees C. and a second peak occurs at about 220 degrees C. As the temperature is increased, more light is released, until about 350 degrees C. At this point, all of the formerly trapped electrons have recombined with copper ions, and no additional light is produced. The exemplary ZnS:Cu semiconductor-doped glass material can then be used again for another radiation dose measurement.

Figure 3:
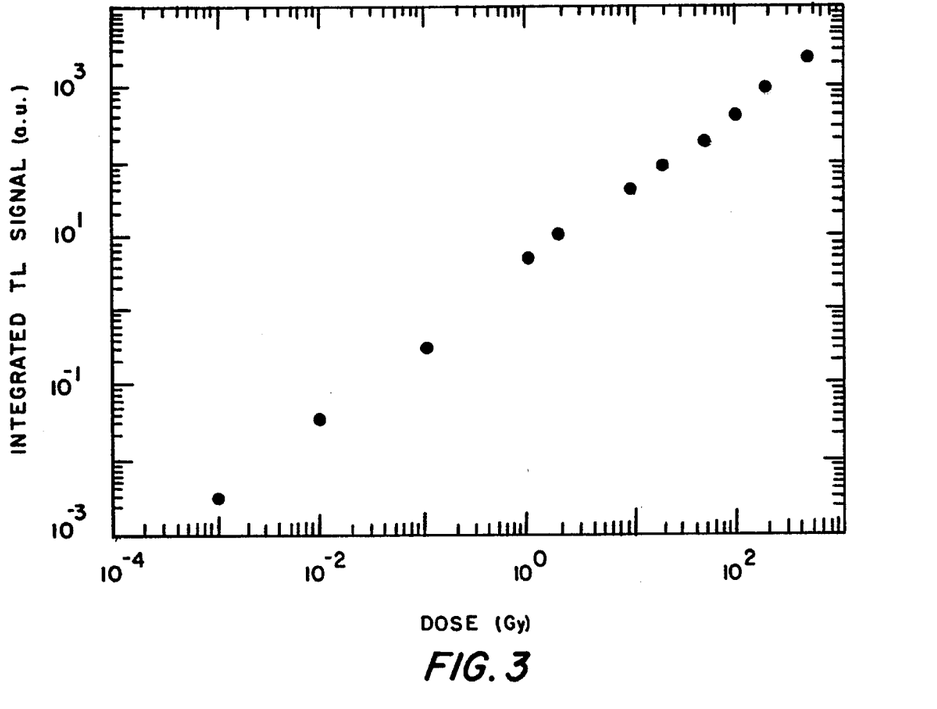
FIG. 3 illustrates the gamma-ray dose dependence of the thermoluminescence of the ZnS:Cu glass dosimeter material used in the invention.

FIG. 3 illustrates the dose-dependent performance of the exemplary thermoluminescent ZnS:Cu glass dosimeter material of the invention. This is a plot of the total thermoluminescent light output as a function of Cobalt 60 gamma ray radiation dose over the range from about $10^{-4}$ gray (Gy) to almost $10^3$ Gy. The thermoluminescent (TL) signal was observed to be linear over a wide range of (almost seven orders of magnitude) of exposures.

Figure 4:
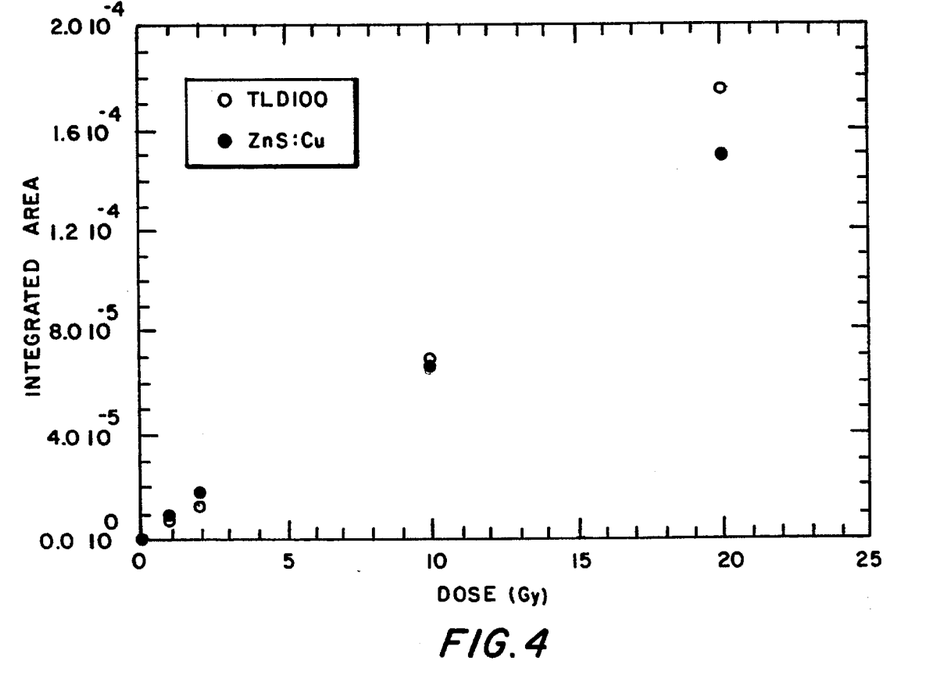
FIG. 4 illustrates a comparison of the performance of the thermoluminescent glass material shown in FIG. 3 with the performance of a well-known, commercially-available dosimeter material, TLD-100.

FIG. 4 shows a comparison of the performance of the thermoluminescent dosimeter glass material ZnS:Cu shown in FIG. 3 with the performance of the well-known dosimeter material TLD-100. As indicated in FIG. 4, the five dark circles represent a plot of the thermoluminescent signal vs Dose in Gy to illustrate the performance of the thermoluminescent glass material ZnS:Cu shown in FIG. 3, whereas the four light circles represent a plot of the thermoluminescent signal vs Dose in Gy to illustrate the performance of the well-known dosimeter material TLD-100. TLD-100 is a lithium fluoride dosimeter which is activated by magnesium and titanium. TLD-100 is a dosimeter with a very good sensitivity which produces a good thermoluminescent signal. As can be seen in FIG. 4, the new ZnS:Cu glass phosphor material of the dosimeter used in the invention has even a better sensitivity than the well-known, dosimeter phosphor TLD-100 material has.

Figure 5:
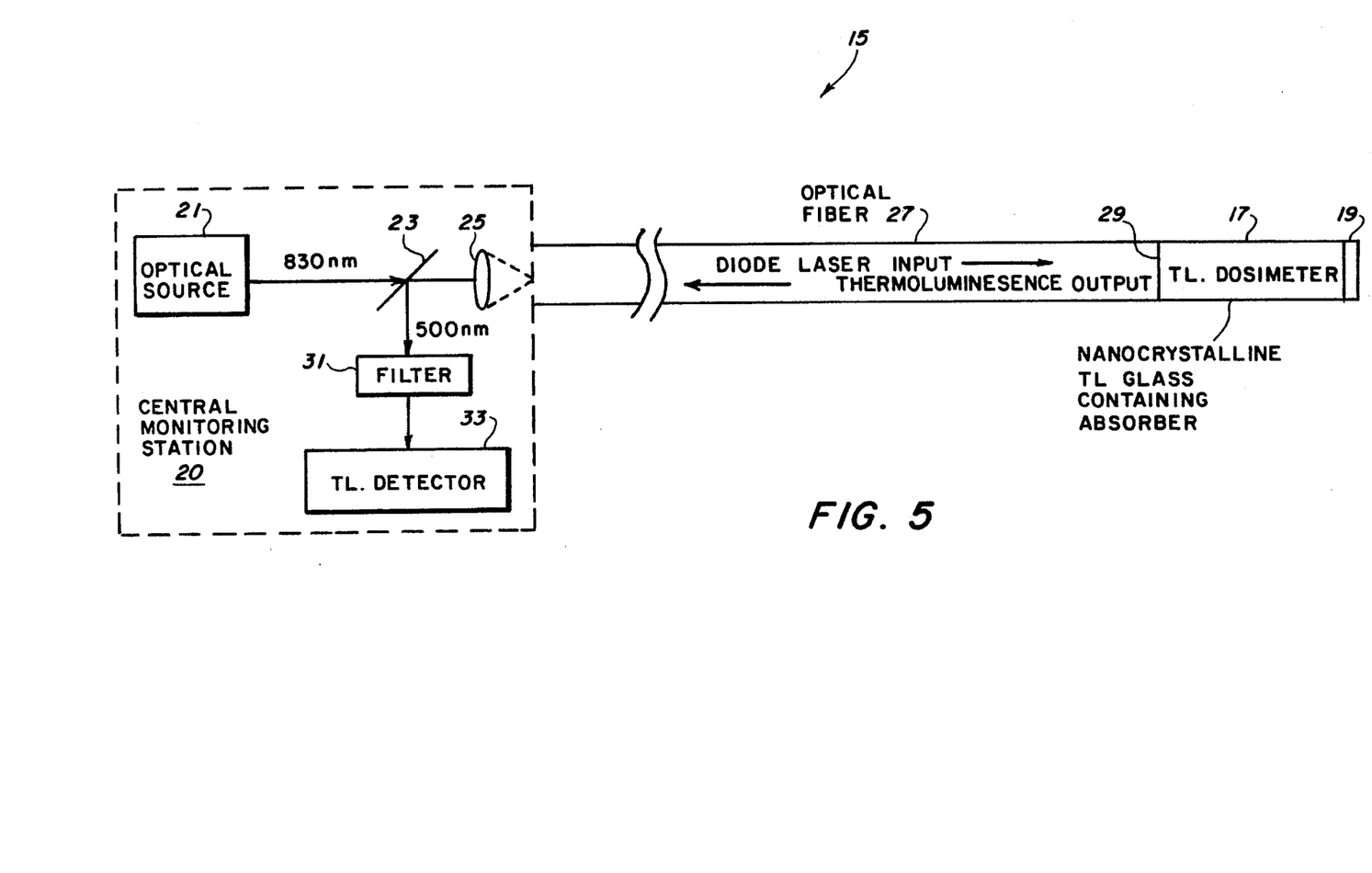
FIG. 5 is a schematic diagram of the thermoluminescent dosimeter system of the invention.

FIG. 5 shows a schematic diagram of the all-optical, rapid readout, thermoluminescent dosimeter system 15 of this invention. The thermoluminescent dosimeter system 15 includes a central monitoring station 20, a remotely positioned, optically-transparent, thermoluminescent (TL) glass dosimeter 17 and an optical fiber or fiberoptic cable 27 which couples the central monitoring station 20 to the TL dosimeter 17. The central monitoring station 20 includes an optical source 21, a dichroic beam splitter 23, a focusing lens 25, a filter 31 and a thermoluminescent (TL) detector 33. It should be understood that a unidirectional fiber splitter or optical coupler could be used in place of the dichroic beam splitter 23 to perform the operation of the dichroic beam splitter 23 (to be explained).

The optically-transparent thermoluminescent (TL) glass dosimeter 17 contains the thermoluminescent glass dosimeter material described above in relation to FIGS. 1–4. In addition, the thermoluminescent glass dosimeter material incorporates an absorber or dopant (not shown), such as Neodymium (Nd), Ytterbium (Yb), or Erbium (Er) rare earth ions, or a combination of such absorbers, to absorb the light energy from the optical source 21 (to be explained). The absorber is chosen to be transparent in the wavelength region of the thermoluminescent emission from the glass dosimeter 17 (to be explained).

The concentration of the absorber (or combination of absorbers) in the TL dosimeter 17 can be adjusted depending on the desired length of the dosimeter 17. High absorber concentrations result in the absorption of all of the light energy from the optical source 21 in a short length of the dosimeter 17. Low concentrations of absorber allow for the use of a longer dosimeter 17.

As an example, a neodymium ion ($Nd^{3+}$) concentration of 4% by weight in the glass dosimeter 17 has an absorption cross section of $\alpha=8$ $cm^{-1}$ at 800 nm. With this concentration, 90% of the 800 nm light from the optical source 21 will be absorbed in a distance of 3 mm. A concentration of 0.4% Nd by weight would provide a 90% absorption length of 30 mm. A concentration of 8% Nd by weight would have a 90% absorption length of 1.5 mm. Rare earth ions often have high fluorescence yields that tend to reduce the heating efficiency. The use of high concentrations reduces the fluorescence yield and enhances the heating efficiency. For the case of the Nd ion dopant, a concentration of between 4% and 7& is desirable.

The material of the thermoluminescent (TL) dosimeter 17 may be in the form of a rod, fiber, plate or tube. An end of the glass dosimeter 17 may contain an optional broadband reflective coating 19.

In the operation of the thermoluminescent dosimeter system 15 of FIG. 5, 0.8 to 10 micron light from the optical source 21 (which may be, for example, a diode laser in the range of 0.8 microns to 10 microns, a gas laser, a molecular laser or a solid state laser) and at an exemplary 830 nanometer (nm) wavelength is passed through the dichroic beam splitter 23 and focused by the lens 25 into the optical fiber or fiberoptic cable 27 which may be, for example, several kilometers in length. The optical fiber 27 is fused at its far end 29 to the dosimeter glass material of the thermoluminescent dosimeter 17 so that the dosimeter glass material effectively becomes a part of the optical fiber 27. Thus, the optical fiber 27 directs light energy from the laser diode 21 to the thermoluminescent material in the TL dosimeter 17. It is preferrable that the TL glass dosimeter 17 and the optical fiber 27 have substantially identical end face configurations at the far end 29 of the optical fiber 27 to maximize the transfer of light energy from the optical fiber 27 into the TL glass dosimeter 17.

The exemplary 830 nm laser light entering the TL glass dosimeter 17 is absorbed efficiently by the rare earth ions in the light-absorbing dopant, selected from, for example, Nd, Yb, or Er, and is transformed into heat. This heat is sufficient to stimulate blue-green thermoluminescence at a wavelength of about 500 nm (as shown in FIG. 1) in the TL glass material in the dosimeter 17 that has been previously irradiated with ionizing radiation from some radiation source (not shown) of, for example, deep ultraviolet, x-ray or gamma radiation.

It should be emphasized at this time that the optical source 21 can be any type of light source (such as the previously-mentioned exemplary diode laser, molecular laser or solid state laser) which can provide light energy at an appropriate light wavelength sufficient to heat the thermoluminescent glass material in the thermoluminescent glass dosimeter 17 to produce thermoluminescent emissions.

The blue-green 500 nm thermoluminescence light in the dosimeter 17 is directed back through the optical fiber 27, collimated by the lens 25 and passed to the dichroic beam splitter 23. When the optional broadband reflective coating 19 is disposed at an end of the glass dosimeter 17, the reflective coating 19 will minimize any loss of thermoluminescence light out of the far end of the dosimeter 17 by reflecting it back to the optical fiber 27, and even more thermoluminescence light will be directed back to the beam splitter 23.

The dichroic beam splitter 23 is designed to transmit the 830 nm semiconductor laser light therethrough and reflect the 500 nm blue-green light from the TL dosimeter 17. The reflected 500 nm TL light is filtered by the filter 31 to remove background light, or photoluminescence from the absorbing species, and is detected by the thermoluminescent detector 33 which is sensitive to light in the range from about 450 nm to about 550 nm. The thermoluminescent detector 33, which may be a photomultiplier tube, a photodiode or any other suitable photodetector, measures the thermoluminescent emissions from the TL glass dosimeter 17.

There are numerous applications for remote radiation dosimetry. Examples of remote radiation dosimetry will now be given in the following discussions of FIGS. 6 and 7.

Figure 6:
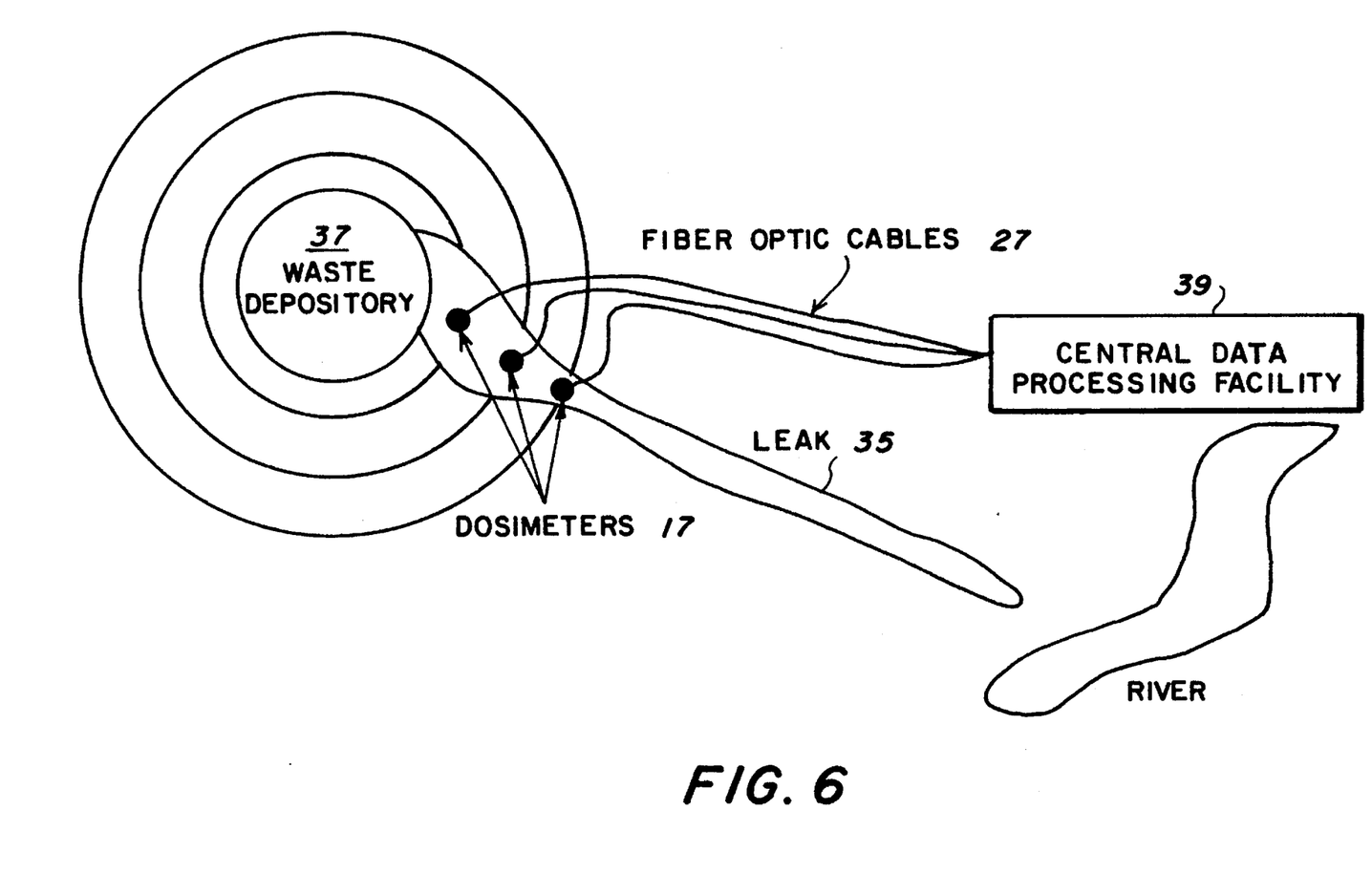
FIG. 6 is a first exemplary application of the thermoluminescent dosimeter system of the invention in the monitoring of nuclear contamination from a waste depository.

FIG. 6 ilustrates a first exemplary application of the thermoluminescent dosimeter system of the invention in the monitoring of nuclear contamination from a waste depository.

Monitoring ground water contamination around nuclear facilities is an important problem. The TL glass dosimeter 17 of FIG. 5 is capable of withstanding harsh environments. As shown in FIG. 6, a series of these fiber-coupled dosimeters 17 could be buried underground at various locations around a nuclear waste storage facility to monitor nuclear waste seepage or a leak 35 from a waste depository 37. The dosimeters 17 could be linked by associated fiberoptic cables to a central monitoring station 39, similar to the central monitoring station 20 in FIG. 1. A computer-controlled X-Y translator (not shown) in the monitoring station 39 could then selectively position each optical fiber to accept the light from the light source 21 (FIG. 5) to selectively interrogate the dosimeters 17 from that central monitoring station 39. This could reduce the cost of various problems associated with sampling nuclear waste materials. The dosimeters 17 are reusable after they are interrogated.

The thermoluminescent emission data that indicates the amount of radiation that the thermoluminescent glass dosimeter system 15 of the invention has been exposed to can be read out any number of times with the diode laser 21 (FIG. 5) to interrogate the system 15. The system 15 can be interrogated hourly, daily, weekly, monthly, yearly, or at any other desired time. It doesn't matter. The thermoluminescent glass material in the dosimeter system 15 is very rugged, so that it can survive being buried for long periods of time. In relation to FIG. 6, the direction of a nuclear leak 35 and the quantity of nuclear contamination can be mapped out by taking several measurements from the different dosimeters 17. In the central data processing facility 39 of FIG. 6, a single diode laser 21 (FIG. 5) and a single thermoluminescent detector 33 (FIG. 5) can be used with the laser light being selectively directed to each of the different fiber optic cables 27, thus drastically reducing the number of diode lasers, to even only one laser diode, to monitor an entire array of dosimeters 15. Thus, only one diode laser 21 (FIG. 5) and only one TL detector 33 (FIG. 5) are required to access a large number of thermoluminescent glass dosimeters 17 disposed in a large area to be monitored, tremendously reducing the cost of the dosimeter system of the invention.

Figure 7:
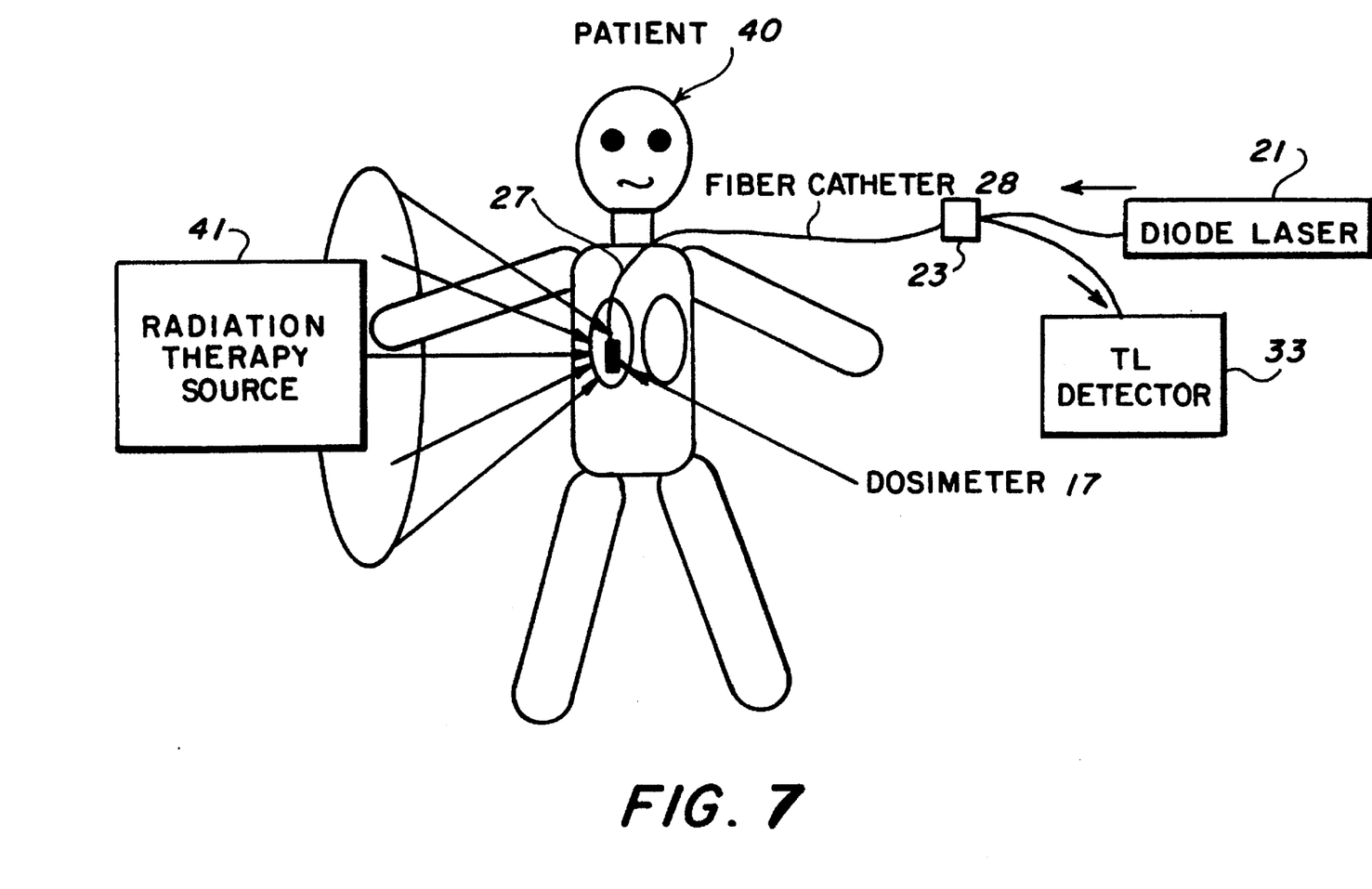
FIG. 7 is a second exemplary application of the thermoluminescent dosimeter system of the invention in an in vivo radiation monitoring of radiation doses in patients undergoing radiation therapy.

FIG. 7 illustrates a second exemplary application of the thermoluminescent dosimeter system of the invention for in vivo radiation monitoring of radiation doses in a patient 40 undergoing radiation therapy.

Monitoring of radiation doses in a patient 40 undergoing radiation therapy can help to improve the effectiveness of radiation treatments. In this application of the thermoluminescent dosimeter system of the invention, the thermoluminescent dosimeter 17 can be spliced to the end of an optical fiber 27 and used in conjunction with a fiber catheter 28 to introduce the dosimeter inside the body of a human patient 40. In this manner, the thermoluminescent dosimeter 17 can be directed to a certain portion of the human body that is being exposed to radiation as, for example, in radiation therapy for cancer treatment. And the dosimeter 17 can be placed next to a tumor that is being irradiated and provide the physician with an immediate feedback as to how much of a radiation dose that he is applying to the tumor during radiation therapy. This would allow more precise control of radiation doses and help reduce collateral damage to healthy tissues.

In addition, the fiber catheter 28 can be left in the body of the patient 40 and disconnected from the laser diode 21 and TL detector 33 by using an optical coupler (not shown). In that way the catheter 28 would only have to be inserted one time and the patient 40 could return to the physician for his weekly treatments. After the treatments have been completed, the catheter 28 could be removed at that time. This reduces the cost of catherization, which is quite expensive.

The New Semiconductor-Doped Glass Material

For a better understanding of the fiber-coupled thermoluminescent dosimeter system of the invention, the new semiconductor-doped glass material that was recently developed by the present inventors will now be discussed. However, the absorbant dopant of Nd, Yb, or Er ions that is added to the new glass material to provide an absorbing medium for the light from the diode laser 21 will not be discussed, since the doping of a material with rare earth ions is well known in the art.

The nanocrystalline inorganic solid/glass composite phosphors are fabricated by deposition of the inorganic solid and the activators within a porous glass matrix. The deposition can be accomplished using known chemical methods for doping glasses, such as, for example, precipitation from a liquid phase solution, or CVD. Often, the most convenient method will be precipitation from a liquid phase solution. The exact deposition process used and the parameters employed for deposition are not critical, provided that the deposited materials are nanocrystalline and the glass retains its porosity. Generally, the size of the deposited crystals is controlled by the pore size of the glass into which the crystals are deposited. The pores restrict the growth of the deposited crystals so that the deposited crystals have a diameter smaller than that of the pore in which they precipitate. However, the pores in a porous glass are in reality tortuous channels, sometimes interconnected, which behave like pores. Thus, if the concentration of the dopants within the glass becomes too great for the average effective pore size, the nanocrystals will grow through the channels, interconnect, and develop into large crystals that reduce the transparency of the glass.

Following the deposition of the inorganic solid and activators, a thermal heat treatment may be used to promote diffusion of the activators in the nanocrystals and to control the nature and quality of the crystalline phase. This heat treatment is performed at a temperature sufficient to substantially enhance diffusion of the activators. Typically, the activation temperature is also selected to partially, or perhaps even fully, consolidate the porous glass. If desired, the porous glass can be activated at a temperature below that needed to consolidate the glass. The activation temperature, however, should not be so high as to liquify the glass. For 7930 Vycor™ glass (Corning, Inc.), an activation temperature of typically from about 800° to about 1100° C. may be used. The activation temperature must be below the melting temperature of the glass. Annealing, i.e., accompanied by at least partial consolidation of the glass (collapsing of at least some of the pores), requires temperatures above the $T_g$ of the glass.

The time for activation may be varied depending upon what, if any, degree of consolidation is required. While the order in which the components are mixed is not critical, all components of the glass, must be present during the activation step.

Suitable porous glasses are amorphous matrices with densely packed, tortuous, nanometer-sized, interconnecting pores or channels. The exact chemical compositon is not critical. One example of such a glass is porous Vycor™ (Corning, Inc.). Vycor™ glass is a 96% silica glass obtained by heat treating a borosilicate glass to separate the boron and silicate phases and then subjecting the heat treated glass to an acid etch, thereby removing most of the boron phase and leaving the porous 96% silica glass. The Vycor™ glass can be obtained in a wide variety of sizes or shapes, including sheets, rods, tubes, and irregular shapes. Suitable porous glass hosts can also be prepared using well-known sol-gel glass technology. These glasses are prepared by the acid catalyzed or base catalyzed hydrolysis of metallic esters or alkoxides. Single component or multiple component glasses can be prepared and include, for example, silicate, titanate, germanate and zirconate glasses. The pore size, distribution of pore sizes and the density of the pores in the sol-gel glass can be controlled by the hydrolysis conditions and by the details of the drying procedure. The porous sol-gel glasses may also be manufactured in a wide variety of shapes and sizes as well as in thin films. Porous glass matrices that may be made by the sol-gel process include pure $SiO_2$, pure $Al_2O_3$ (alumina glass), pure $TiO_2$ and mixtures thereof in varying proportions to provide glasses with varying properties.

In the starting glasses to be doped with nanocrystalline semiconductor particles (nanocrystals) and at least one activator therefor, the pores typically average about 10 to about 100 Å in diameter, more often about 40 to about 75 Å in diameter and most often about 40 to about 50 Å in diameter. Vycor glass™ (Corning 7930) has an average pore size of about 40 Å diameter. Average pore sizes of less than 40 Angstrom diameter can be obtained using sol-gel derived glasses. Average pore sizes of less than 10 Å diameter are not practical because it is difficult to diffuse solutions into the pores. Average pore sizes that are larger than 100 Å in diameter may be too large to assure nanocrystal formation, depending on the concentration of the activator and semiconductor employed. The optical quality of glasses prepared from larger pore sizes is diminished. Additionally, the size distribution of the particles should be selected to minimize the number of particles with diameters greater than 100 Å. Particles having a diameter of greater than 100 Å reduce the transparency of the glass matrix.

A pore density of 25 to 30 volume percent is ideal because it allows for the formation of isolated and separated nanocrystalline structures. If the void volume is too high, the semiconductor crystallites may be too close together and merge to form particles larger than nanocrystals. Lower pore densities simply reduce the amount of semiconductor material that can be introduced to the glass. This situation may be desirable for certain applications such as doped fiber-optic cables.

The nanocrystalline nature of the semiconductor particles in the material of the present invention is critical. Because of the small size of nanocrystals, glass doped therewith maintains its transparency. If the nanocrystals are sufficiently small (below about 80 Å, with a narrow size distribution so that few, if any particles are more than 120 Å) they may become quantum-confined. The effects of this quantum confinement are favorable in many circumstances, although quantum-confined semiconductor particles are not required to obtain many benefits of the present invention.

The selection of suitable inorganic solid phosphor materials to be deposited in porous glass in an effort to fabricate nanocrystalline phosphor/glass composites is guided by previous knowledge about the most useful and efficient bulk phosphors. There have been literally thousands of different types of phosphors manufactured using many combinations of inorganic solids and activators. Some of the most useful phosphors are sulfides of zinc or alkaline earths such as calcium, magnesium and strontium, activated with transition metal or rare earth ions. Activated ZnS phosphors have found wide utility in a variety of applications including cathodoluminescence, radioluminescence, electro—luminescence, and IR sensitivity. Different activators and/or co-activators have been identified and their relative concentrations optimized for the desired application. For example, useful ZnS phosphors have been manufactured using activators and co-activators (when required) selected from the following: rare earth ions, silver, copper, lead, chloride, and manganese ions. This list is by no means complete.

Sufficient activator or (activator/co-activator) should be employed in the glass to provide an activator concentration effective to luminescently activate the semiconductor nanocrystals, i.e., render the nanocrystalline semiconductor particles capable of emitting light in the visible or infrared range in response to electronic excitation at an appropriate wavelength.

Figure 8:
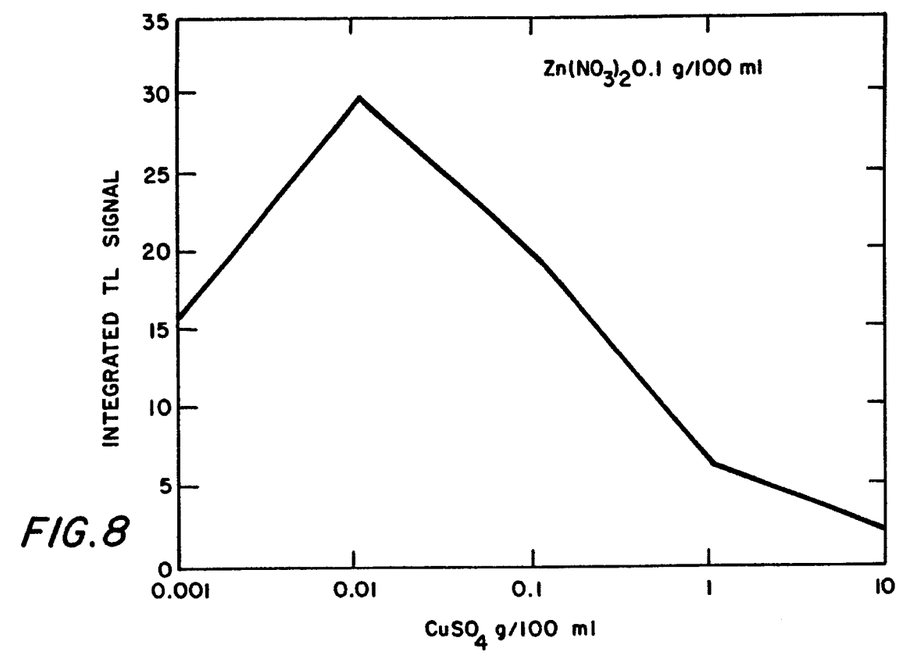
FIG. 8 shows the thermoluminescence signal as a function of copper sulfate concentration for a sample made according to the procedures of Example 1, but with varying concentrations of copper sulfate in the copper sulfate doping solution.
Figure 9:
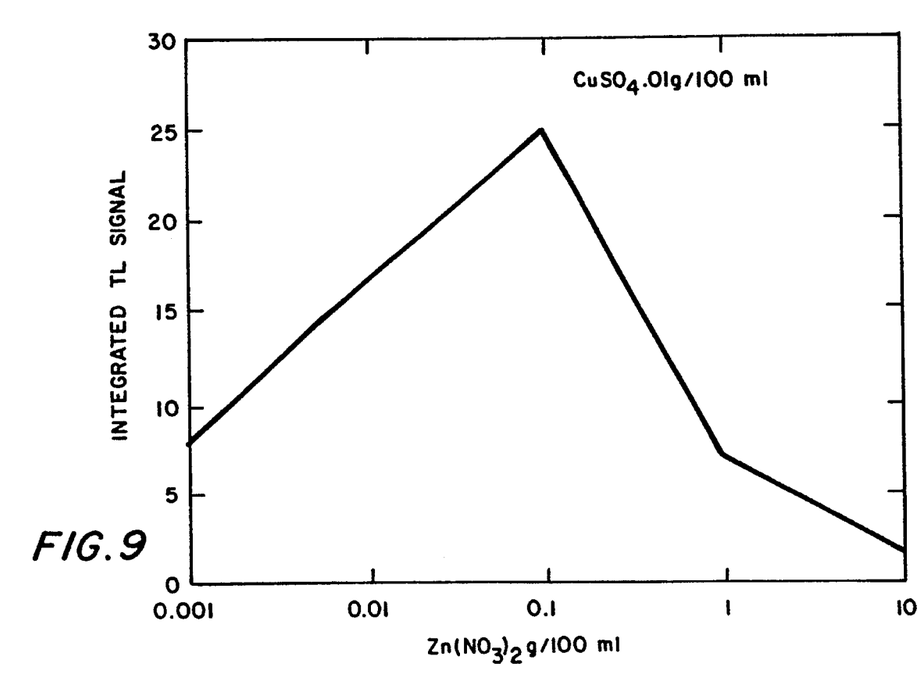
FIG. 9 shows the thermoluminescence signal as a function of zinc nitrate concentration for a sample made according to Example 1, but with varying concentrations of zinc nitrate in the zinc nitrate doping solution.
Figure 10:
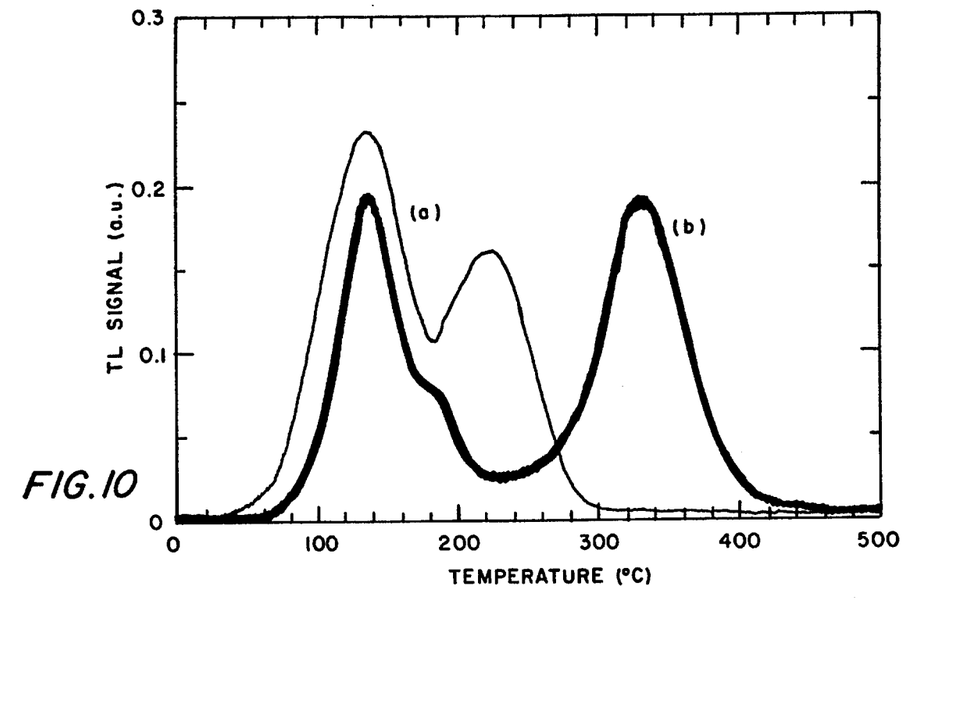
FIG. 10 shows the effect of ZnS concentration on the positions of the thermoluminescence glow peaks. Curve (a) shows the typical thermoluminescence observed at low concentrations (corresponding to 1 g/100 ml zinc nitrate in the doping solution) of copper activated (1 mg Cu/ml doping solution) ZnS nanocrystals in Vycor™ glass, while curve (b) shows the growth of a higher temperature glow peak in a higher concentration (corresponding to 10 g/100 ml zinc nitrate in the doping solution) of copper activated (1 mg Cu/ml doping solution) ZnS nanocrystals in Vycor™ glass.

The concentrations and identities of the dopants result in different physical and optical properties of the nanocrystalline semiconductor doped glass. For example, copper activated zinc sulfide glasses display the following trends:

increasing the concentration of copper sulfate in the doping solution from zero to approximately 0.1 gram in 100 cubic centimeters of water shows an increase in thermoluminescence with increasing copper concentration. As the concentration of copper is increased further, the thermoluminescence intensity decreases (FIG. 8).

high concentrations of ZnS lead to a decrease in the thermoluminescence emission from the glass (FIG. 9). Intermediate concentrations of ZnS lead to thermoluminescent glow peaks at higher temperatures (FIG. 10).

These tendencies may be characteristic of all doped glass compositions according to the above discussion. At low concentrations, increasing dopant levels increase the number of luminescent crystals, thus increasing the overall luminescence. As the concentration of the activator and/or semiconductor becomes too high, the crystals grow too large and the glass loses transparency and luminescence. At intermediate concentration of semiconductors, the luminescent nanocrystalline semiconductors particles may communicate with each other, slightly changing their electronic energy levels and characteristic spectra. Also, to maintain the transparancy of the glass to its own fluorescence, the activator should not form particles of greater than 100 Å in the glass. Possibly, but not necessarily, the activator may substitute into the crystal lattice of the nanocrystalline semiconductor particles. However, activation might be the result of proximity effects between the activator and the nanocrystalline semiconductor particles.

The activated nanocrystalline inorganic solid phosphors may be manufactured, for example, from type II–VI semiconductors, of which ZnS is an example, type III–V semiconductors, of which gallium arsenide is an example, type IV—IV semiconductors, of which silicon is an example, alkali halides, of which potassium chloride is an example, or alkaline earth sulfides, of which calcium sulfide is an example. The activator and/or co-activator ions can be chosen from the rare earth metals, of which europium is an example, or the transition metals, of which manganese is an example. Co-activators also often include halogen ions, of which chloride is an example. The use of europium as an activator results in a mixed blue and red luminescence.

Doped glasses according to the above discussion can exhibit cathodoluminescence, electroluminescence, thermoluminescence, radioluminescence or sensitized luminescence. The emission of light after excitation can be immediate or delayed (energy trapping). The exact type of luminescence observed will depend, in a characteristic way, upon the semiconductor and activator used, as well as the concentration of those materials within the glass. The type of luminescence observed depends on the excitation conditions. The chemistry of the phosphor may be manipulated and predicted to enhance a particular type of luminescence.

The following description is a generalized exemplary procedure for making a doped glass according to the above discussion. The purpose of this generalized procedure is illustrative only. Although the doping method illustrated is precipitation from solution, it should be understood that other doping methods, dopants and porous glasses may be used.

In a typical doping procedure, a piece of porous glass, such as porous Vycor™ glass, is immersed in an aqueous solution of a water soluble metal salt such as zinc nitrate. The solution is allowed to diffuse completely throughout the porous glass. The metal salt solution concentration can range between zero and the solubility limit of the salt (1.8 grams per cubic centimeter of water for zinc nitrate). If a metal sulfide dopant, such as zinc sulfide, is desired it may be formed in situ, for example, by the addition of an aqueous solution of thioacetamide to the solution of the water-soluble salt. The thioacetamide/metal salt solution reaction proceeds for a period of time ranging from one hour to several days, depending on the temperature of the solution. A lower temperature (about 25° C. to about 50° C.) results in a slower reaction and assures a uniform distribution of metal sulfide throughout the porous glass piece. An alternative method for producing a metal sulfide is to expose the metal doped glass piece to hydrogen sulfide ($H_2S$) gas for a period of approximately one hour. The $H_2S$ gas diffuses quickly throughout the porous glass and reacts with the deposited metal salt. The porous glass, containing the desired dopant is next immersed in an aqueous solution of metal salt activator, such as copper sulfate or europium chloride. The concentration of the metal salt activator can range between zero and the solubility limit of the salt (approximately 0.4 grams per cubic centimeter for copper sulfate, although no enhancement beyond about 0.2 g/ml is observed in the case of copper sulfate). This solution is allowed to diffuse throughout the porous glass, typically at about room temperature. The glass is then dried slowly, over a period of one hour, to prevent cracking of the glass.

The temperature is raised slowly (several hours) to approximately 300 degrees centigrade and then the temperature is increased more rapidly (one hour) to typically no greater than about 1100° C.–1150° C. The glass is maintained at high temperature for a period of three to 24 hours to fully activate the glass phosphor. The glass is cooled to room temperature over a period of one to three hours. The resulting glass is highly luminescent when exposed to radiation wavelengths that overlap the absorption band of the doped, activated glass. For ZnS activated with copper, exposure to ultraviolet wavelengths of less than 300 nm, results in an intense blue-green luminescence.

Having described the thermoluminescent dosimeter materials that can be used in the thermoluminescent dosimeter system of the invention, the following examples are given to illustrate specific applications of those dosimeter materials including the best mode now known for the performance of those materials. These specific examples are not intended to limit the scope of the application of those materials described herein.

EXAMPLES

Example 1—Zinc sulfide/copper doping 0.1 g of zinc nitrate hexahydrate were dissolved in 100 ml distilled water. To the resulting solution were added 1 cc concentrated nitric acid. 1 g of porous Corning 7930 Vycor™ glass were then added to the acidified solution, in which it was allowed to remain for 1 to 2 hours to allow complete diffusion of the zinc nitrate solution throughout the glass. The glass was then removed from the solution and dried.

A thioacetamide solution was prepared by dissolving 1.0 g thioacetamide in 100 ml distilled water, adding 1 ml concentrated nitric acid. The thioacetamide solution was then placed in a constant temperature bath set to 30° C. The dried zinc-loaded porous glass was then placed into the sulfide solution and allowed to react therewith for at least 10 hours to form nanocrystalline ZnS. The porous glass sample was then removed from solution and dried.

0.01 g copper sulfate was dissolved in 100 ml water. The zinc sulfide-containing glass sample was then placed in the copper sulfate solution and allowed to remain there for 1 to 2 hours to allow complete diffusion of the copper sulfate solution throughout the porous glass. The copper doped zinc sulfide glass sample was then removed from the copper sulfate solution and dried.

The dried zinc sulfide/copper-doped porous glass was then placed in an oven at room temperature. The oven temperature was then increased at a rate of about 1° C./minute up to a temperature of 300° C. Over the course of an next hour, the temperature of the oven was then raised to 1150° C. The sample was baked at 1150° C. for at least 3 hours and then allowed to cool to room temperature (Cooling may occur either by shutting off the oven and allowing the sample to cool within, or by removing the sample from the oven).

Figure 11:
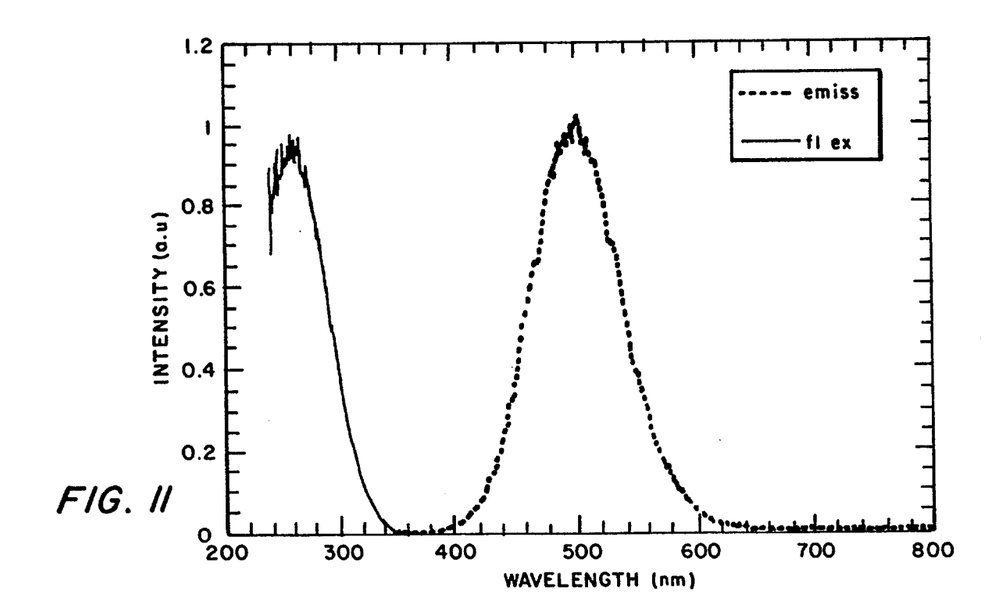
FIG. 11 shows the excitation and emission spectra of a copper activated ZnS/Vycor™ glass composite phosphor made according to Example 1.

The absorption spectrum of the ZnS phosphor glass exhibited a maximum at approximately 260 nm, with a broad tail extending to approximately 320 nm. This absorption feature was characteristic of excitonic absorption within ZnS nanocrystallites (quantum dots). The location of the absorption peak reflected the blue shift of the exciton energy due to quantum confinement of the excitons. The width of the absorption feature reflected the size distribution of the quantum dots in the glass composite. After excitation of the nanocrystalline phosphor by the UV light, transfer of the energy to the copper ion activators occurs. Emission occurs from the excited copper ions. The emission is characterized by a broad band centered at approximately 500 nm, similar to that from a bulk copper activated ZnS phosphor. The quantum efficiency of the emission is also similar to that of the bulk phosphor. The temporal decay of the emission is faster than that of the bulk phosphor emission. FIG. 11 shows the emission and fluorescence excitation spectra of a sample of the copper activated ZnS quantum dot phosphor composite. The solid curve was obtained by scanning the optical excitation source from 240 nm to 350 nm and monitoring the total emission. The heavy dashed curve is the emission curve obtained by exciting the sample at 266 nm. An elemental analysis of the sample indicated that the individual concentrations of zinc sulfide and copper were less than 5 ppm.

Example 2—KCl Activated with Auropium Ions, Manufactured in Porous Vycor Glass

The procedure used in Example 1 was used, except that the glass was directly doped using a solution of 1 g KCl in 100 ml of water followed by doping with 1 g EuCl solution in 100 ml of water. No sulfides were used.

Figure 12:
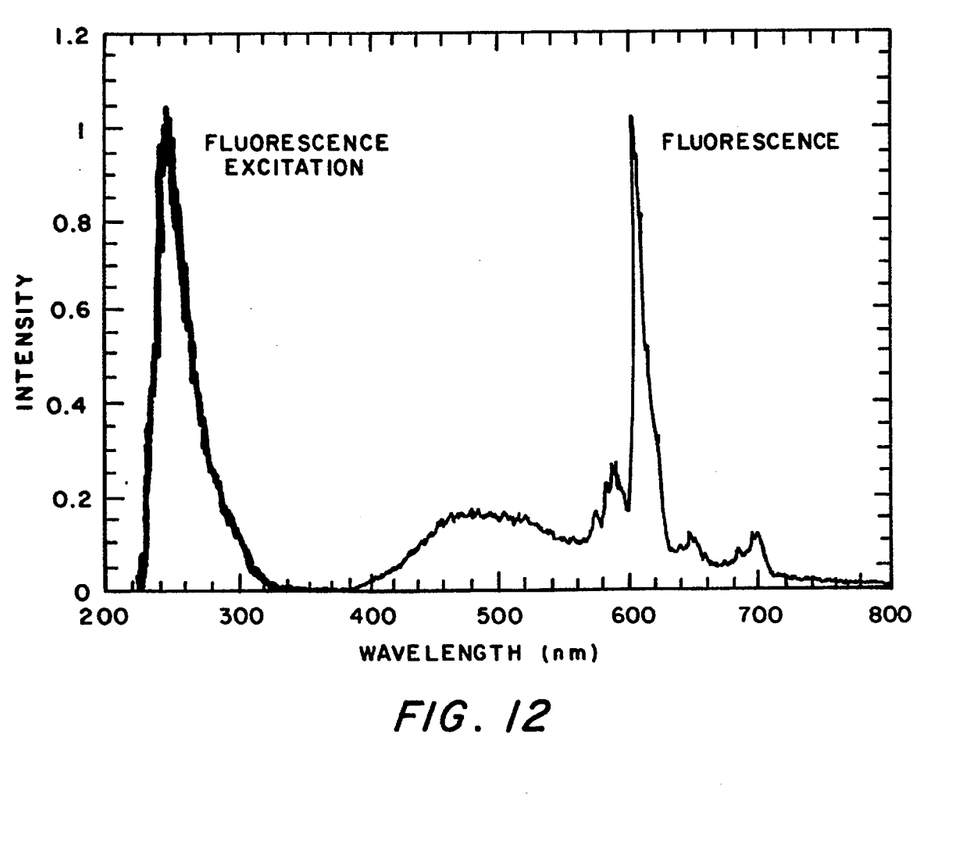
FIG. 12 shows the excitation and emission curve of a europium activated KCl/Vycor™ glass composite phosphor made according to Example 2.

The absorption spectrum of the KCl phosphor glass exhibited a maximum at approximately 240 nm, with a broad tail extending to approximately 300 nm. This absorption feature was characteristic of absorption by europium ions within the crystal lattice of the alkali halide. The location and width of the absorption peak reflect the nature and the influence of the crystalline host environment seen by the europium ions. After excitation of the nanocrystalline phosphor by the UV light, emission occurs from the excited europium ions. The emission is characterized by a broad band centered at approximately 450 nm due to emission from $Eu^{+2}$ ions, in addition to a narrow peak at 615 nm due to $Eu^{+3}$ emission. The emission and fluorescence excitation spectra are shown in FIG. 12. The heavy solid curve was obtained by scanning the optical excitation source from 224 nm to 350 nm and monitoring the total emission. The light solid curve is the emission spectrum obtained by exciting the sample at 266 nm.

Advantages and New Features of the Fiber-Coupled Thermoluminescent Dosimeter System of the Invention The thermoluminescent dosimeter system described above is an all-optical radiation sensing system. The thermoluminescent glass material in the dosimeter system is sensitive to ionizing radiation. The readout of the material is photothermally stimulated by heat that results from the absorption of semiconductor laser light by an absorbing material, such as rare earth ions for example, incorporated into the thermoluminescent (TL) glass dosimeter material. The laser light is directed to the TL material by way of a fiberoptic cable. The TL material is transparent to the TL emission wavelengths (420 nm–550 nm) and this light is directed back to a TL detector by way of the same fiberoptic cable.

The thermoluminescent dosimeter system offers fast, in-situ readout. The glass dosimeter material does not have to be placed in a separate TL machine for analysis.

The dosimeter material is optically transparent to the TL emission wavelengths. The glass dosimeter material can be any arbitrary size or shape, thus increasing the sensitivity of the TL glass dosimeter.

The TL dosimeter system is fiberoptically coupled.

The TL dosimeter system can be operated by remote control, thus minimizing the exposure of workers to radiation sources.

The TL glass dosimeter of the TL dosimeter system can be placed in severe environments and will withstand temperatures in excess of 800 degrees C. The TL glass dosimeter is not moisture sensitive and can withstand corrosive environments.

The TL glass dosimeter material is inexpensive, easy to synthesize and achieves reproducible performance.

Alternatives

A number of other activated nanocrystalline semiconductor materials can be used for the dosimeter material including ZnSe, CdS, CdSe, as well as other materials.

An alternative geometry can be used that consists of a hollow tube of activated semiconductor nanocrystallites in a silica glass matrix. A solid rod of rare-earth-ion-doped glass is placed inside the hollow tube. The two glass units are heated and drawn into a fiber. The end result is a rare-earth-ion-doped glass core fiber surrounded by the activated semiconductor-doped glass thermoluminescent material. The fiber is spliced to the end of a commercial optical fiber. A semiconductor laser is used to heat the core fiber. Heat from the core radiates outward and heats the thermoluminescent material, resulting in the emission of light. The thermally emitted light is coupled into the optical fiber as in the configuration described above and directed back to a TL detector.

Alternative heating methods include: an electrical heating source, thermochemical heating, inductive heating, or ultrasonic heating. Temperature measurement can be done optically if an ion such as europium is used in the dosimeter material. The relative peak heights and positions of the emission wavelengths are sensitive to temperature and can be used as a temperature measuring scheme. For many applications, it is not necessary to know the temperature, only the total integrated light output signal is used to determine the radiation dose.

Therefore, what has been described in a preferred embodiment of the invention is a thermoluminescent radiation dosimeter system comprising: a radiation-sensitive thermoluminescent dosimeter which utilizes a new, semiconductor-doped glass material disposed at a remote location for storing energy from ionizing radiation when exposed thereto and for releasing the stored energy in the form of thermoluminescence light at a first wavelength when stimulated by exposure to light energy at a predetermined stimulating second wavelength; an optical source for providing stimulating light energy at the predetermined stimulating second wavelength; a thermoluminescent detector for measuring thermoluminescent emissions; and an optical fiber for passing the predetermined stimulating light energy from the optical source to the thermoluminescent dosimeter to stimulate the thermoluminescent dosimeter to produce thermoluminescence light from stored energy and for passing the thermoluminescence light to the thermoluminescent detector to enable the thermoluminescent detector to measure any thermoluminescent emissions occuring when the thermoluminescent dosimeter is heated by the light energy at the predetermined stimulating second wavelength.

It should therefore readily be understood that many modifications and variations of the present invention are possible within the purview of the claimed invention. It is therefore to be understood that, within the scope of the appended claims, the invention may be practiced otherwise than as specifically described.

What is claimed and desired to be secured by Letters Patent of the United States is:

1. A thermoluminescent radiation dosimeter system for the remote monitoring of radiation sources, said system comprising:

a radiation-sensitive thermoluminescent dosimeter disposed at a remote location for storing energy from ionizing radiation when exposed thereto and for releasing the stored energy in the form of thermoluminescence light at a first wavelength when stimulated by exposure to light energy at a predetermined stimulating second wavelength, said thermoluminescent dosimeter including: an optically transparent glass matrix material doped with nanocrystalline semiconductor particles; and a metal activator within said optically transparent glass matrix material for said nanocrystalline semiconductor particles, said metal activator being present in a concentration effective to thermoluminescently activate said nanocrystalline semiconductor particles when said thermoluminescent dosimeter is stimulated by stimulating light energy at the predetermined stimulating second wavelength, said doped glass matrix material being transparent to its thermoluminescent emissions;

an optical source for providing stimulating light energy at the predetermined stimulating second wavelength;

a thermoluminescent detector for measuring thermoluminescent emissions at the first wavelength; and an optical fiber for passing the predetermined stimulating light energy from said optical source to said thermoluminescent dosimeter to stimulate said thermoluminescent dosimeter to produce thermoluminescence light from stored energy and for passing the thermoluminescence light to said thermoluminescent detector to enable said thermoluminescent detector to measure any thermoluminescent emissions occuring when the thermoluminescent dosimeter is heated by the light energy at the predetermined stimulating second wavelength.

2. The thermoluminescent radiation dosimeter system of claim 1 wherein said doped optically transparent glass matrix material further includes:

an absorber dopant for absorbing the stimulating light energy at the predetermined stimulating second wavelength to cause said nanocrystalline semiconductor particles to heat up and stimulate thermoluminescence emissions from the stored energy from ionizing radiation.

3. The thermoluminescent radiation dosimeter system of claim 2 wherein:

said absorber dopant is selected from the group consisting of erbium, neodymium, ytterbium and mixtures thereof.

4. The thermoluminescent radiation dosimeter system of claim 2 wherein:

said doped glass matrix material emits thermoluminescent light in the visible or infrared spectrum immediately after absorption of the stimulating light energy at the predetermined stimulating second wavelength.

5. The thermoluminescent radiation dosimeter system of claim 2 wherein:

said doped glass matrix material forms trapped electrons upon absorption of ionizing radiation, and emits thermoluminescent light in the visible or infrared spectrum after the detrapping of said trapped electrons by being heated by the stimulating light energy.

6. The thermoluminescent radiation dosimeter system of claim 5 wherein:

said doped glass matrix material detraps said trapped electrons upon exposure to infrared radiation.

7. The thermoluminescent radiation dosimeter system of claim 1 wherein:

said nanocrystalline semiconductor particles are selected from the group consisting of II–VI and III–V semiconductors.

8. The thermoluminescent radiation dosimeter system of claim 7 wherein:

said nanocrystalline semiconductor particles can be selected from the group consisting of ZnS, ZnSe, CdS, CdSe and GaP; and said metal activator can be selected from the group consisting of transition metal ions, rare earth ions, and halide ions.

9. The thermoluminescent radiation dosimeter system of claim 8 wherein:

said activator can be selected from the group consisting of $Cu^{+1}$ and $Cl^-$.

10. The thermoluminescent radiation dosimeter system of claim 1 wherein:

said optical source provides the predetermined stimulating second wavelength at a light wavelength sufficient to heat said doped glass matrix material to cause said thermoluminescent dosimeter to produce thermoluminescent emissions.

11. The thermoluminescent radiation dosimeter system of claim 1 wherein:

said optical source is selected from the group consisting of a diode laser, a molecular laser and a solid state laser.

12. The thermoluminescent radiation dosimeter system of claim 1 wherein:

said optical source is selected from the group consisting of a discharge lamp and a light emitting diode.

* * * * *